(12) United States Patent
Bar-Or et al.

(10) Patent No.: US 8,512,548 B2
(45) Date of Patent: *Aug. 20, 2013

(54) MEASUREMENT AND USES OF OXIDATIVE STATUS

(75) Inventors: David Bar-Or, Englewood, CO (US); Raphael Bar-Or, Denver, CO (US)

(73) Assignee: Luoxis Diagnostics, Inc., Greenwood Village, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/601,586

(22) Filed: Aug. 31, 2012

(65) Prior Publication Data

US 2012/0325685 A1 Dec. 27, 2012

Related U.S. Application Data

(60) Division of application No. 12/625,072, filed on Nov. 24, 2009, which is a continuation-in-part of application No. 12/121,945, filed on May 16, 2008.

(60) Provisional application No. 60/938,925, filed on May 18, 2007.

(51) Int. Cl.
*G01N 27/26* (2006.01)

(52) U.S. Cl.
USPC .............................................. 205/792; 435/4

(58) Field of Classification Search
None
See application file for complete search history.

(56) References Cited

U.S. PATENT DOCUMENTS

| | | | |
|---|---|---|---|
| 4,299,919 | A | 11/1981 | Jellinek |
| 5,290,519 | A | 3/1994 | Bar-Or et al. |
| 5,395,755 | A | 3/1995 | Thorpe et al. |
| 5,679,532 | A | 10/1997 | Repine |
| 6,177,260 | B1 | 1/2001 | Benzie et al. |
| 6,269,261 | B1 | 7/2001 | Ootomo |
| 6,429,021 | B1 | 8/2002 | Qian et al. |
| 7,063,782 | B2 | 6/2006 | Wayment et al. |
| 7,125,723 | B2 | 10/2006 | Popov et al. |
| 7,132,296 | B2 | 11/2006 | Ou et al. |
| 7,134,602 | B2 | 11/2006 | Harima |
| 2005/0142613 | A1 | 6/2005 | Bar-Or et al. |
| 2005/0244983 | A1 | 11/2005 | Ching |
| 2007/0020181 | A1 | 1/2007 | Workman et al. |
| 2009/0004686 | A1 | 1/2009 | Bar-Or et al. |
| 2010/0267074 | A1 | 10/2010 | Bar-Or et al. |

FOREIGN PATENT DOCUMENTS

| | | |
|---|---|---|
| RU | 2241997 | 12/2004 |
| WO | WO 03/071266 | 8/2003 |
| WO | WO 2004/068140 | 8/2004 |
| WO | WO 2007/039775 | 4/2007 |
| WO | WO 2007/059455 | 5/2007 |

OTHER PUBLICATIONS

Alonso De Vega et al., "Oxidative Stress in Critically Ill Patients with Systemic Inflammatory Response Syndrome," Critical Care Medicine, vol. 30, No. 8 (Aug. 2002), pp. 1782-1786, (Abstract).
Alonso De Vega et al., "Plasma Redox Status Relates to Severity in Critically Ill Patients," Critical Care Medicine, vol. 28, No. 6 (Jun. 2000), pp. 1812-1814, (Abstract).
Ascensão et al., "Biochemical Impact of a Soccer Match—Analysis of Oxidative Stress and Muscle Damage Markers Throughout Recovery," Clinical Biochemistry, vol. 41, No. 10-11 (Jul. 2008), pp. 841-851, (Abstract).
Author Unknown, "Universal Reduction-Oxidation (REDOX) electrode for the Temporal Measurement of the Redox Potential Health and Disease," VCU Technology Transfer Marketing Flyer, as early as Apr. 12, 2007, 1 page, available at www.research.vcu.edu/ott/licensable_technologies/flash/05-70_ward.htm.
Bar-Or et al., "Heterogeneity and Oxidation Status of Commerical Human Albumin Preparations in Clinical Use," Critical Care Medicine, Jul. 2005, vol. 33, No. 7, pp. 1638-1641.
Bar-Or et al., "Heterogeneity and Oxidation Status of Commerical Human Albumin Preparations in Clinical Use," Critical Care Medicine, vol. 33, No. 7 (Jul. 2005), pp. 1638-1641, (Abstract).
Bayir et al., "Assessment of Antioxidant Reserves and Oxidative Stress in Cerbrospinal Fluid after Severe Traumatic Brain Injury in Infants and Children," Pediatric Research, 2002, vol. 51(5), pp. 571-578.
Biffl et al., "Plasma from Aged Stored Red Blood Cells Delays Neutrophil Apoptosis and Primes for Cytotoxicity: Abrogation by Poststorage Washing but not Prestorage Leukoreduction," The Journal of Trauma, vol. 50, No. 3 (Mar. 2001), pp. 426-432, (Abstract).
Brittingham et al., "Febrile Transfusion Reactions Caused by Sensitivity to Donor Leukocytes and Platelets," Journal of the American Medical Association, vol. 165, No. 7 (Oct. 19, 1957), pp. 819-825, (Abstract).
Carballal et al., "Sulfenic Acid Formation in Human Serum Albumin by Hydrogen Peroxide and Peroxynitrite," Biochemistry, vol. 42 (2003), pp. 9906-9914.
Cases et al., "Response of antioxidant defences to oxidative stress induced by prolonged exercise: antioxidant enzyme gene expression in lymphocytes," European Journal of Applied Physiology, vol. 98, No. 3 (Oct. 2006), pp. 263-269.

(Continued)

*Primary Examiner* — Jon P Weber
*Assistant Examiner* — Robert Yamasaki
(74) *Attorney, Agent, or Firm* — Sheridan Ross P.C.

(57) ABSTRACT

The present invention provides a method of determining the overall oxidative status of a body fluid or a tissue of a patient by measuring the oxidation-reduction potential (ORP) of the body fluid or tissue. The method has been found to be useful in the diagnosis, evaluation and monitoring of patients who have suffered a trauma (such as a head injury), patients suspected of being critically-ill or who are critically ill, patients who have an infection, and patients suspected of having a myocardial infarction (MI) or who have had an MI. The method has also been found useful in monitoring and evaluating exercise performance in patients. In addition, the method has been found useful in monitoring and evaluating stored blood products and patients who will receive such a product.

5 Claims, No Drawings

(56) References Cited

OTHER PUBLICATIONS

Cernak et al. "Characterization of Plasma Magnesium Concentration and Oxidative Stress Following Graded Traumatic Brain Injury in Humans," Journal of Neurotrauma, Jan. 2000, vol. 17, No. 1, pp. 53-68.

Codd et al., "Redox Maintenance and Organ Preservation," Transplantation Proceedings, vol. 9, No. 3 (Sep. 1977), pp. 1569-1571, (Abstract).

Codd et al., "Redox Maintenance in Restoration of Organ Viability," The Journal of Surgical Research, vol. 22, No. 5 (May 1977), pp. 585-592, (Abstract).

Collins et al., "Optimal Redox Electrode Potential for 24-Hour Rabbit Kidney Perfusion," The Journal of Surgical Research, vol. 39, No. 3 (Sep. 1985), pp. 246-250, (Abstract).

Cowley et al., Plasma antioxidant potential in sever sepsis: A comparison of survivors and nonsurvivors, Critical Care Medicine, vol. 24, No. 7 (Jul. 1996), pp. 1179-1183, available at www.ccmjournal.com/pt/re/ccm/fulltext.00003246-199607000-00019htm;jsessionid=F2GT . . . .

Dosek et al., "High Altitude and Oxidative Stress," Respiratory Physiology & Neurobiology, vol. 158, No. 2-3 (Sep. 30, 2007), pp. 128-131, (Abstract).

Elokda et al., "Effects of Exercise Training on the Gluthathione Antioxidant System," European journal of Cardiovascular Prevention and Rehabilitation : Official Journal of the European Society of Cardiology, Working Groups on Epidemiology & Prevention and Cardiac Rehabilitation and Exercise Physiology, vol. 14, No. 5 (Oct. 2007), pp. 630-637, (Abstract).

Ferretti et al., "Copper-induced Oxidative Damage on Astrocytes: Protective Effect Exerted by Human High Density Lipoproteins," Biochimica et biophysica acta, vol. 1635, No. 1 (Nov. 30, 2003), pp. 48-54.

Ferretti et al., "Paraoxonase Activity in High-Density Lipoproteins: A Comparison between Health and Obese Females," The Journal of Clinical Endocrinology & Metabolism, vol. 90, No. 3 (Mar. 2005), pp. 1728-1733.

Ferretti et al., "Protective Effect of Paroxonase Activity in High-density Lipoproteins Against Erythrocyte Membranes Peroxidation: A Comparison Between Healthy Subjects and Type 1 Diabetic Patients," The Journal of Clinical Endocrinology and Metabolism, vol. 89, No. 6 (Jun. 2004), pp. 2957-2962.

Galley et al., "Xanthine Oxidase Activity and Free Radical Generaton in Patients with Sepsis," Critical Care Medicine, vol. 24, No. 10 (Oct. 1996), pp. 1649-1653, (Abstract).

Ghiselli et al., "Total Antioxidant Capacity as a Tool to Assess Redox Status: Critical View and Experimental Data," Free Radical Biology & Medicine, vol. 29, No. 11 (Dec. 2000), pp. 1106-1114, (Abstract).

Gomez-Cabrera et al., "Moderate Exercise in an Antioxidant: Upregulation of Antioxidant genes by Training," Free Radical Biology & Medicine, vol. 44, No. 2 (Jan. 15, 2008), pp. 126-131, (Abstract).

Goode et al., "Decreased Antioxidant Status and Increased Lipid Perosidation in Patients with Septic Shock and Secondary Organ Dysfunction," Critical Care Medicine, vol. 23, No. 4 (Apr. 1995), pp. 646-651, (Abstract).

Green et al., "Effluent Redox Potential: A Rapid Method for Assaying Warm Ischemic Injury," The Journal of Surgical Research, vol. 25, No. 3 (Sep. 1978), pp. 222-225, (Abstract).

Horton, "Free Radicals and Lipid Peroxidation Mediated Injury in burn Trauma: The Role of Antioxidant Therapy," Toxicology, vol. 189, No. 1-2 (Jul. 15, 2003), pp. 75-88, (Abstract).

Huang et al., "The Chemistry behind Antioxidant Capacity Assays," Journal of Agriculture and Food Chemistry, vol. 53 (2005), pp. 1841-1856.

Jellinek et al., "Electrochemical Control of Redox Potential in Perfusate for Prolonged Heart Storage," Transactions—American Society for Artificial Internal Organs, vol. 20 (1974), pp. B:533-537, (Abstract).

Jellinek et al., "Oxidation-Reduction Maintenance in Organ Preservation," Archives of Surgery, vol. 120, No. 4 (Apr. 1985), pp. 439-442, (Abstract).

Ji, "Antioxidants and Oxidative Stress in Exercise," Proceedings of the Society for Experimental Biology and Medicine, Society for Experimental Biology and Medicine (New York, N.Y.), vol. 222, No. 3 (Dec. 1999), pp. 283-292.

Ji, "Modulation of Skeletal Muscle Antioxidant Defense by Exercise: Role of Redox Signaling," Free Radical Biology & Medicine, vol. 44, No. 2 (Jan. 15, 2008), pp. 142-152 (Abstract).

Kohen et al., "Noninvasive in vivo evaluation of skin antioxidant activity and oxidation status," Methods in Enzymology, vol. 300 (1999), pp. 428-437.

Kohen et al., "Quantification of the overall reactive oxygen species scavenging capacity of biological fluids and tissues," Free Radical Biology & Medicine, vol. 28, No. 6 (Mar. 15, 2000), pp. 871-879.

Kyparos et al., "Short Duration Exhaustive Aerobic Exercise Induces Oxidative Stress: A Novel Play-oriented Volitional Fatigue Test," The Journal of Sports Medicine and Physical Fitness, vol. 47, No. 4 (Dec. 2007), pp. 483-490, (Abstract).

Lamprecht et al., "Single Bouts of Exercise Affect Albumin Redox State and Carbonyl Groups on Plasma Protein of Trained Men in a Workload Dependent Manner," Journal of Applied Physiology, vol. 104, No. 6 (Jun. 2008), pp. 1611-1617, (Abstract).

Lekhi et al., "Influence of Exercise on Oxidant Stree Products in Elite Indian Cyclists," British Journal of Sports Medicine, vol. 41, No. 10 (Oct. 2007), pp. 691-693, (Abstract).

Lemineur et al., "Biomarkers of oxidative stress in critically ill patients: What should be measured, when and how?" Curr. Opin. Clin. Nutr. Metabol. Care, Nov. 2006, vol. 9(6), pp. 704-710.

Margonis et al., "Oxidative Stress Biomarkers Responses to Physical Overtraining: Implications for Diagnosis," Free Radical Biology and Medicine, vol. 43, No. 6 (Sep. 15, 2007), pp. 901-910, (Abstract).

Mayer et al., "Reduced serum total reductive capacity in lethal severe trauma," The Journal of Trauma, vol. 51, No. 1 (Jul. 2001), pp. 88-91.

McAnulty et al., "Influence of Carbohydrate, Intense Exercise , and Rest Intervals on Homonal and Oxidative Changes," International Journal of Sport Nutrition and Exercise Metabolism, vol. 17, No. 5 (Oct. 2007), pp. 478-490, (Abstract).

Meijer, "Exercise-induced oxidative stress in older adults as measure by antipyrine oxidation," Metabolism, vol. 50, No. 12 (Dec. 2001), pp. 1484-1488, (Abstract).

Michailidis et al., "Sampling Time is Critical for Measurement of Aerobic exercise-induced oxidative Stress," Medicine and Science in Sports and Exercise, vol. 39, No. 7 (Jul. 2007), pp. 1107-1113, (Abstract).

Miller et al., "Acute Respiratory Distress Syndrome in Blunt Trauma: Identification of Independent Risk Factors," The American Surgeon, vol. 68, No. 10 (Oct. 2002), pp. 845-851, (Abstract).

Miller et al., "Improved Myocardial Preservation by Control of the Oxidation-Reduction Potential," The Journal of Heart Transplantation, vol. 4, No. 3 (May 1985), pp. 319-324, (Abstract).

Nikolaidis et al., "Decreased Blood Oxidative Stress After Repeated Muscle-Damaging Exercise," Medicine and Science in Sports and Exercise, vol. 39, No. 7 (Jul. 2007), pp. 1080-1089, (Abstract).

Paschalis et al., "Uniform and Prolonged Changes in Blood Oxidative Stress After Muscle-damaging Exercise," In vivo (Athens, Greece), vol. 21, No. 5 (Sep.-Oct. 2007), pp. 877-883, (Abstract).

Prior et al., "In Vivo Total Antioxident Capacity: Comparison of Different Analytical Methods," Free Radical Biology & Medicine, vol. 27, Nos. 11-12 (1999), pp. 1173-1181.

Prokhorov et al., "A method of redoxometry in clinical studies," Vopr. Med. Khim., vol. 35, No. 5 (Sep.-Oct. 1989), pp. 2-6, (Abstract).

Radak et al., "Effects of Exercise on Brain Function: Role of Free Radicals," Applied Physiology, Nutrition, and Metabolism, vol. 32, No. 5 (Oct. 2007), pp. 942-946, (Abstract).

Radak et al., "Exercise, Oxidative Stress and Hormesis," Ageing Research Reviews, vol. 7, No. 1 (Jan. 2008), pp. 34-42, (Abstract).

Radak et al., "Systemic Adaptation to Oxidative Challenge Induced by Regular Exercise," Free radical Biology & Medicine, vol. 44, No. 2 (Jan. 15, 2008), pp. 153-159, (Abstract).

Rael et al., "Combined cupric-and cuprous-binding peptides are effective in preventing IL-8 release from endothelial cells and redox reactions," Biochemical and Biophysical Research Communications, vol. 357 (2007), pp. 543-548.

Rael et al., "Oxidation-reduction potential and paraxonase-arylesterase activity in trauma patients," Biochemical and Biophysical Research Communications, vol. 361 (2007), pp. 561-565.

Rael et al., "Plasma oxidation-reduction potential and protein oxidation in traumatic brain injury," J. Neurotrauma, Aug. 2009, vol. 26(8), pp. 1203-1211.

Rael et al., "The effect of storage on the accumulation of oxidative biomarkers in donated packed red blood cells," J. Trauma, Jan. 2009, vol. 66(1), pp. 76-81.

Rahnama et al., "Oxidative Stress responses in Physical Education Students During 8 Weeks Aerobic Training," The Journal of Sports Medicine and Physical Fitness, vol. 47, No. 1 (Mar. 2007), pp. 119-123, (Abstract).

Rana et al., "Study on Oxidative Stress in Patients with Abdominal Trauma," Molecular and Cellular Biochemistry, vol. 291, No. 1-2 (Oct. 2006), pp. 161-166, (Abstract).

Rao et al., "Redox Potential Measurements of Plasma in Patients Undergoing Coronary Artery Bypass Graft and Its Clinical Significance," Journal of Pharmacological and Toxicological Methods, vol. 38 (1997), pp. 151-156.

Rice-Evans, "Measurement of Total Antioxidant Activity as a Marker of Antioxidant Status in Vivo: Procedures and Limitations," Free Radical Research, vol. 33, Supplement (Nov. 2000), pp. 59-66, (Abstract).

Rosenberg et al. "Who bounces back? Physiologic and other predictors of intensive care unit readmission," Critical Care Medicine, Mar. 2001, vol. 29, No. 3, pp. 511-518.

Roth et al., "Assessing the antioxidative status in critically ill patients," Current Opinion in Clinical Nutrition and Metabolic Care, vol. 7 (2004), pp. 161-169.

Sauaia et al., "Early Predictors of Postinjury Multiple Organ Failure," Archives of Surgery, vol. 129, No. 1 (Jan. 1994), pp. 39-45, (Abstract).

Sen et al., "Antioxidants in Exercise Nutrition," Sports Medicine (Auckland, N.Z.), vol. 31, No. 13 (2001), pp. 891-898, (Abstract).

Shin et al., "Exercise Training Improves the Antioxidant Enzyme Activity with no Change of Telomere Length," Mechanisms of Ageing and Development, vol. 129, No. 5 (May 2008), pp. 254-260, (Abstract).

Shing et al., "The Effect of Consecutive Days of Exercise on Markers of Oxidative Stress," Applied Physiology, Nutrition, and Metabolism, vol. 32, No. 4 (Aug. 2007), pp. 677-685, (Abstract).

Soffler, "Oxidative Stress," The Veterinary Clinics of North America. Equine Practice, vol. 23, No. 1 (May 2007), pp. 135-157 (Abstract).

Steinberg et al., "Cytokine and Oxidative responses to Maximal Cycling Exercise in Sedentary Subjects," Medicine and Science in Sports and Exercise, vol. 39, No. 6 (Jun. 2007), pp. 964-968, (Abstract).

Veglia et al., "Age- and gender-related oxidative status determined in healthy subjects by means of OXY-SCORE, a potential new comprehensive index," Biomarkers, vol. 11, No. 6 (Nov.-Dec. 2006), pp. 562-573.

Vollard et al., "Exercise-induced oxidative stress: Myths, realities and physiological relevance," Sports Med., 2005, vol. 35(12), pp. 1045-1062.

Williams et al., "Dietary Supplements and Sports Performance: Introduction and Vitamins," Journal of the International Society of Sports Nutrition, vol. 1, No. 2 (2004), pp. 1-6.

Winterbourn et al., "Protein Carbonyl Measurements Show Evidence of Early Oxidative Stress in Critically Ill Pateints," Critical Care Medicine, vol. 28, No. 1 (Jan. 2000), pp. 275-277 (Abstract).

Zoppi et al., "Overreaching-induced oxidative stress, enhanced HSP72 expression, antioxidant and oxidative enymes downregulaltion," Scandinavian Journal of Medicine & Science in Sports, vol. 18, No. 1 (Feb. 2008), pp. 67-76 (Abstract).

Written Opinion for International (PCT) Patent Application No. PCT/US08/63855, mailed Aug. 26, 2008, 8 pages.

International Search Report for International (PCT) Patent Application No. PCT/US08/63855, mailed Aug. 26, 2008, 3 pages.

International Preliminary Report on Patentability for International (PCT) Patent Application No. PCT/US08/63855, mailed Nov. 24, 2009, 10 pages.

Extended European Search Report for European Patent Application No. 08755661.9, dated Aug. 3, 2010, 7 pages.

Gubler et al. "Trauma Recidivism in the Elderly," The Journal of Trauma: Injury, Infection, and Critical Care, Dec. 1996, vol. 41, No. 6, pp. 952-956.

MEASUREMENT AND USES OF OXIDATIVE STATUS

This application is a division of pending U.S. patent application Ser. No. 12/625,072, filed Nov. 24, 2009, which is a continuation-in-part of pending U.S. patent application Ser. No. 12/121,945, filed May 16, 2008, which claims the benefit of Provisional Patent Application No. 60/938,925, filed May 18, 2007, the complete disclosures of which are incorporated herein by reference.

FIELD OF THE INVENTION

The invention relates to a method of determining the overall oxidative status of a body fluid or a tissue of a patient by measuring the oxidation-reduction potential (ORP) of the body fluid or tissue. In particular, the invention relates to methods for the diagnosis, evaluation and monitoring of patients who have suffered a trauma (such as a head injury), patients suspected of being critically-ill or who are critically ill, patients who have an infection, and patients suspected of having a myocardial infarction (MI) or who have had an MI. The invention also relates to methods for the evaluation and monitoring of the exercise performance of patients. The invention further relates to methods for the evaluation and monitoring of stored blood products and of patients who will receive such products.

BACKGROUND

Oxidative stress is caused by a higher production of reactive oxygen and reactive nitrogen species or a decrease in endogenous protective antioxidative capacity. Oxidative stress has been related to various diseases and aging, and it has been found to occur in all types of critical illnesses. See, e.g., Veglia et al., *Biomarkers*, 11(6): 562-573 (2006); Roth et al., *Current Opinion in Clinical Nutrition and Metabolic Care*, 7:161-168 (2004); U.S. Pat. No. 5,290,519 and U.S. Patent Publication No. 2005/0142613. Several investigations have shown a close association between the oxidative status of a critically ill patient and the patient's outcome. See Roth et al., *Current Opinion in Clinical Nutrition and Metabolic Care*, 7:161-168 (2004).

Oxidative stress in patients has been evaluated by measuring various individual markers. See, e.g., Veglia et al., *Biomarkers*, 11(6): 562-573 (2006); Roth et al., *Current Opinion in Clinical Nutrition and Metabolic Care*, 7:161-168 (2004); U.S. Pat. No. 5,290,519 and U.S. Patent Publication No. 2005/0142613. However, such measurements are often unreliable and provide conflicting and variable measurements of the oxidative status of a patient. See Veglia et al., *Biomarkers*, 11(6): 562-573 (2006); Roth et al., *Current Opinion in Clinical Nutrition and Metabolic Care*, 7:161-168 (2004). The measurement of multiple markers which are then used to provide a score or other assessment of the overall oxidative status of a patient has been developed to overcome the problems of using measurements of single markers. See Veglia et al., *Biomarkers*, 11(6): 562-573 (2006); Roth et al., *Current Opinion in Clinical Nutrition and Metabolic Care*, 7:161-168 (2004). Although such approaches are more reliable and sensitive than measurements of a single marker, they are complex and time consuming. Thus, there is a need for a simpler and faster method for reliably measuring the overall oxidative status of a patient.

BRIEF DESCRIPTION OF THE INVENTION

The present invention provides such a method. In particular, the invention provides a method of determining the overall oxidative status of a body fluid or a tissue of a patient by measuring the oxidation-reduction potential (ORP) of the body fluid or tissue. The method has been found to be useful in the diagnosis, evaluation and monitoring of patients who have suffered a trauma (such as a head injury), patients suspected of being critically-ill or who have been diagnosed as being critically ill, patients who have an infection, and patients suspected of having a myocardial infarction (MI) or who have been diagnosed as having an MI. The method has also been found useful in monitoring and evaluating exercise performance in patients. In addition, the method has been found useful in monitoring and evaluating stored blood products and patients who will receive such a product.

DETAILED DESCRIPTION OF THE PRESENTLY PREFERRED EMBODIMENTS OF THE INVENTION

As used herein, "patient" means a mammal, such as a dog, cat, horse, cow or human. Most preferably, the patient is a human.

Any body fluid of a patient can be used in the method of the invention. Suitable body fluids include a blood sample (e.g., whole blood, serum or plasma), urine, saliva, cerebrospinal fluid, tears, semen, vaginal secretions, amniotic fluid and cord blood. Also, lavages, tissue homogenates and cell lysates can be utilized and, as used herein, "body fluid" includes such preparations. Preferably, the body fluid is blood, plasma, serum or cerebrospinal fluid. For head injuries, the body fluid is most preferably cerebrospinal fluid or plasma. In cases other than head injuries, the body fluid is most preferably plasma.

Any tissue of a patient can be used in the method of the invention. Suitable tissues include skin, eye and mouth tissues and tissue from biopsies.

As used herein, "normal," "normal patient" or "control" means a mammal of the same species as the patient (e.g., the normal will be a human when the patient is a human), and who is not suffering from any disease. Since ORP increases with age, normals should be of the same age or age range as the patient(s) being tested.

An oxidation-reduction system, or redox system, involves the transfer of electrons from a reductant to an oxidant according to the following equation:

$$\text{oxidant} + ne^- \leftrightarrow \text{reductant} \quad (1)$$

where $ne^-$ equals the number of electrons transferred. At equilibrium, the redox potential (E), or oxidation-reduction potential (ORP), is calculated according to the Nernst-Peters equation:

$$E(ORP) = E_o - RT/nF \ln [\text{reductant}]/[\text{oxidant}] \quad (2)$$

where R (gas constant), T (temperature in degrees Kelvin) and F (Faraday constant) are constants. $E_o$ is the standard potential of a redox system measured with respect to a hydrogen electrode, which is arbitrarily assigned an $E_o$ of 0 volts, and n is the number of electrons transferred. Therefore, ORP is dependent on the total concentrations of reductants and oxidants, and ORP is an integrated measure of the balance between total oxidants and reductants in a particular system. As such, ORP provides a measure of the overall oxidative status of a body fluid or tissue of a patient.

An ORP measurement which is significantly higher than that of normals will indicate the presence of oxidative stress. Oxidative stress has been related to many diseases, and it has been found to occur in all types of critical illnesses. Accordingly, an ORP level significantly higher than that of normals indicates the presence of a disease and perhaps a critical illness. An ORP measurement which is the same as or lower than that of normals indicates the absence of oxidative stress and the absence of a disease or critical illness. Thus, the ORP level of a patient can be used by a medical doctor or veterinarian as an aid in diagnosing or ruling out the presence of a disease, particularly a serious illness. Sequential measurements of ORP over time can be used to monitor the progression of a disease and the effectiveness or lack of effectiveness of treatment of the disease. If a patient's ORP does not decrease after treatment, or especially if it increases despite treatment, this may indicate a poor prognosis and the need for more aggressive and/or additional and/or different treatments. In the case of a measurement made by a patient, such as a patient experiencing symptoms of myocardial infarction, the ORP level may indicate the need for the patient to see a doctor or to immediately proceed to an emergency room for treatment.

The ORP of a body fluid or a tissue can be easily measure by contacting an ORP or redox electrode with the body fluid or tissue. Such electrodes are available commercially from, e.g., Microelectrodes, Inc., Bedford, N.H. Such electrodes can suffer from day-to-day variability, and the use of references standards will be necessary. Suitable references standards include saturated quinhydrone at several pH's. The electrode is connected to a meter which provides a readout of the ORP in millivolts and, optionally, other parameters, such as pH and temperature. Such meters are available commercially from, e.g., Hanna Instruments, Woonsocket, R.I.

The method of the invention has been found to be useful in the diagnosis, evaluation and monitoring of patients who are suffering from, or who are suspected of having, certain diseases. ORP can be used, in combination with a medical history, symptoms and other test results, as an aid in diagnosing, evaluating and monitoring these diseases and treatments of them. In particular, a normal ORP may be very helpful in ruling out the presence of a disease, particularly a serious illness, and in saving medical resources that might otherwise be devoted to unnecessarily treating patients. In addition, a significantly high ORP (indicating oxidative stress) may be used to identify those patients who are in need of immediate or more aggressive treatment of their disease and/or treatment to reduce oxidative stress.

An ORP that is significantly high compared to normals may indicate the need or desirability of performing tests for one or more individual markers of oxidative stress to better understand the reason or source of, and therefore the best treatment for, the oxidative stress or disease. Thus, the invention also includes the use of ORP in combination with tests for one or more individual markers of oxidative stress (collectively referred to herein as an "oxidative stress panel of tests"). Such markers of oxidative stress and methods of measuring them are known. See, e.g., Veglia, et al., *Biomarkers*, 11(6):562-573 (2006); Rana et al., *Mol. Cell Biochem.*, 291:161-166 (2006); Roth et al., *Curr. Opin. Clin. Nutr. Metab. Care*, 7:161-168 (2004); Horton, *Toxicology*, 189:75-88 (2003); Winterbourn et al., *Crit. Care Med.*, 28:143-149 (2000); Ghiselli et al., *Free Radic. Biol. Med.*, 29(11):1106-1114 (2000); Rice-Evans, *Free Radic. Res.*, 33 Suppl.: S59-566 (2000); Prior and Cao, *Free Radic. Biol. Med.*, 27(11-12):1173-1181 (1999); Galley et al., *Crit. Care Med.*, 24:1649-53 (1996); Goode et al., *Crit. Care Med.*, 23:646-651 (1995), the complete disclosures of which are incorporated herein by reference.

Trauma injury is a leading cause of death and disability for all age groups under 60 years of age. In the United States, trauma injuries account for more than 160,000 deaths each year and millions more survivable injuries. For many people, the injury causes temporary pain and inconvenience. For others, the injury leads to suffering, disability, chronic pain, and a profound change in quality of life, including substantial financial consequences. The economic costs of trauma injuries include the costs associated with medical treatment as well as lost productivity costs. In 2000 alone, the 50 million injuries that required medical treatment will ultimately cost $406 billion. This includes estimates of $80.2 billion in medical care costs and $326 billion in productivity losses.

The method of the present invention has been found to be useful in the diagnosis, evaluation and monitoring of patients who have suffered a trauma. As used herein, "trauma" refers to physical injury to any part of a patient's body or to multiple parts of a a patient's body. Trauma injuries include head injuries, internal injuries, blunt trauma, multiple trauma, broken bones and burns.

The present invention provides a means for the determination and monitoring of the oxidative status of traumatized patients and provides medical doctors and veterinarians with real-time information to guide trauma treatment and care. In particular, the existence and degree of oxidative stress in traumatized patients can be determined and monitored. For example, an ORP level that is statistically the same as, or lower than, that of normals upon first examination of a trauma patient (e.g., by a paramedic in the field or by a medical doctor in an emergency room) indicates that oxidative stress is not present and that the patient may not need aggressive treatment or may not even need to be admitted to a hospital. In this manner, medical resources can be saved and costs lowered. On the other hand, an ORP level significantly higher than that of normals upon first examination of a trauma patient indicates the presence of oxidative stress and the need for immediate treatment of the patient and for continued monitoring of the patient's ORP. The higher the ORP level, the higher the level of oxidative stress, and the greater the need for aggressive treatment of the patient. An ORP level that decreases with treatment indicates that the patient is improving and that the treatment is working. An ORP level that increases despite treatment indicates that the patient is getting worse and that more aggressive treatment, additional treatment and/or a different treatment is needed. An ORP level that has decreased to the point where it is no longer significantly higher than that of normals indicates that the patient may be discharged from the hospital. Of course, the ORP level is only one diagnostic parameter, and it should be used in combination with other symptoms, results of a physical examination, a medical history, and the results of any other laboratory tests, to determine the proper treatment for a trauma patient.

The method of the invention has also been found to be useful in the diagnosis, evaluation and monitoring of patients who have an infection (e.g., a viral infection or a bacterial infection). Viral infections include infections caused by human immunodeficiency virus, encephalitis virus, hepatitis viruses, herpes viruses, influenza viruses, pneumonia virus and other viruses that cause serious viral illnesses. Bacterial infections include sepsis, pneumonia and numerous other infections.

In a patient suffering from an infection, an ORP level that is statistically the same as, or lower than, that of normals upon examination of such a patient indicates that oxidative stress is not present and that the patient may need only standard treatments. On the other hand, an ORP level significantly higher than that of normals upon examination of a patient indicates the presence of oxidative stress and the need for more aggressive treatment of the patient, including possibly hospital admission, and for continued monitoring of the patient's ORP. The higher the ORP level, the higher the level of oxidative stress, and the greater the need for aggressive treatment of the patient. An ORP level that decreases with treatment indicates that the patient is improving and that the treatment is working. An ORP level that increases despite treatment indicates that the patient is getting worse and that more aggressive treatment, additional treatment and/or a different treatment is needed. An ORP level that has decreased to the point where it is no longer significantly higher than that of normals indicates that aggressive treatment of the patient may be discontinued, including discharge of the patient from the hospital. Of course, the ORP level is only one diagnostic parameter, and it should be used in combination with other symptoms, results of a physical examination, a medical history, and the results of any other laboratory tests, to determine the proper treatment for a patient having an infection.

Each year in the United States, approximately 6-8 million people present to a hospital emergency room (ER) with chest pain or other cardiac symptoms (e.g., shortness of breath and pain or tingling in the left arm). Unfortunately, about 2-5% of the 3-4 million that are sent home from the ER are mistakenly diagnosed. Chest pain diagnostic errors are the leading cause of emergency medicine malpractice awards. Of the other 3-4 million that are hospitalized, about 60-75% do not have cardiac disease. The minimum cost for each hospitalized patient is $3,000-5,000, which means that over 6 billion healthcare dollars are wasted each year because of these unnecessary hospitalizations. With a non-diagnostic electrocardiogram (ECG), reliable early biomarkers do not exist. Troponin I or troponin T levels are unreliable during the first 6-24 hours after the onset of symptoms due to low sensitivity, and creatine kinase isoenzymes (CK-MB) and myoglobin are not cardiac specific. It would be highly desirable to have a laboratory test result that could aid in the diagnosis of serious heart disease (e.g., myocardial infarction or acute coronary syndrome) or rule it out. It would also be highly desirable to have a laboratory test result that could aid in the evaluation and monitoring of patients already diagnosed with heart disease, including assessment of the prognosis of heart patients, gauging the response to treatment, and adjusting treatment of patients in a timely fashion. The method of the invention provides such a test.

In particular, the method of the invention has been found to be useful in the diagnosis, evaluation and monitoring of patients suspected of having a myocardial infarction (MI). The method of the present invention is particularly useful for the early diagnosis of MI. By "early diagnosis" is meant ascertaining the presence or absence of MI during the first few hours (less than 24 hours, especially less than 12 hours) following the onset of symptoms indicative of MI, such as chest pain, shortness of breath and pain or tingling in the left arm. The method of the invention also has been found to be useful in the evaluation and monitoring of patients who have been diagnosed with an MI.

In particular, the existence and degree of oxidative stress in patients presenting with symptoms of MI can be determined and monitored according to the present invention. For example, an ORP level that is statistically the same as, or lower than, that of normals upon first examination of a suspected MI patient (e.g., by a paramedic in the field or by a medical doctor in an emergency room) indicates that oxidative stress is not present and that the patient is not experiencing an MI. In such a case, the patient may not need treatment and may not need to be kept in an ER or admitted to the hospital. In this manner, medical resources can be saved and costs lowered. On the other hand, an ORP level significantly higher than that of normals upon first examination of a suspected MI patient indicates the presence of oxidative stress and that the patient may experiencing an MI. Such an ORP level indicates the need for immediate treatment of the patient and continued monitoring of the patient's ORP. The higher the ORP level, the higher the level of oxidative stress, and the greater the need for aggressive treatment of the patient. An ORP level that decreases with treatment indicates that the patient is improving and that the treatment is working. An ORP level that increases despite treatment indicates that the patient is getting worse and that more aggressive treatment, additional treatment and/or a different treatment is needed. An ORP level that has decreased to the point where it is no longer significantly higher than that of normals indicates that the patient may be discharged from the hospital. Of course, the ORP level is only one diagnostic parameter, and it should be used in combination with other symptoms, results of a physical examination, a medical history, and the results of any other laboratory tests, to determine the proper treatment for a suspected MI patient or a patient diagnosed as actually experiencing an MI.

The method of the invention should also be useful in the diagnosis, evaluation and monitoring of patients who are suffering from, or who are suspected of having, cardiovascular diseases other than myocardial infarction. These other cardiovascular diseases include acute coronary syndrome, artherosclerosis, heart failure, high blood pressure, stroke, transient ischemic attack, impaired circulation, heart disease, cholesterol and plaque formation, ischemia, ischemia reperfusion injury, cardiac disease (e.g., risk stratification of chest pain and interventional procedures), peripheral vascular disease, cardiopulmonary resuscitation, and kidney failure.

The method of the invention has also been found to be useful in the diagnosis, evaluation and monitoring of patients suspected of being critically ill and evaluation and monitoring of patients who are found to be critically ill. A "critical illness" is a disease or condition requiring admission of a patient to an intensive or intermediate care unit, a disease or condition in which death is possible or imminent, a disease or condition that has caused two or more organ system failures, and/or a disease or condition requiring vital organ function support including mechanical ventilation for a patient suffering from the disease or condition. Critical illnesses include systemic inflammatory response syndrome (SIRS), trauma, burn injury, acute pancreatitis, heart attack, heart failure, acute coronary syndrome, stroke, cancer, lung injury, liver injury, kidney failure, severe diabetes, shock, acute respiratory distress syndrome (ARDS), severe infections (e.g., sepsis, influenza and AIDS), and multiple organ failure. It is well known that the presence of oxidative stress in critically ill patients is positively correlated with poor outcomes. See Roth et al., *Curr. Opin. Clin. Nutr. Metab. Care,* 7:161-168 (2004). Accordingly, the ORP of patients who are, who are suspected of being, or who are likely to become, critically-ill should be monitored. An ORP level of a patient that is statistically the same as, or lower than, that of normals indicates that oxidative stress is not present and that the patient is not critically ill. Such an ORP level indicates that aggressive treatment of the patient is not needed. An ORP level that is significantly higher than that of normals indicates the presence of oxidative stress and that the patient is critically ill. Such an ORP level indicates the need for aggressive treatment of the patient and for continued monitoring of the patient's ORP. The higher the ORP level, the higher the level of oxidative stress, and the greater the need for aggressive treatment of the patient. An ORP level that decreases with treatment indicates that the patient is improving and that the treatment is working. An ORP level that increases despite treatment indicates that the patient is getting worse and that more aggressive treatment, additional treatment and/or a different treatment is needed. An ORP level that has decreased to the point where it is no longer significantly higher than that of normals indicates that the patient is no longer critically ill and may be discharged from the hospital. Of course, the ORP level is only one diagnostic parameter, and it should be used in combination with other symptoms, results of a physical examination, a medical history, and the results of any other laboratory tests, to determine the proper treatment for a patient.

The rate of unscheduled hospital readmissions is an important quality indicator often associated with medical mistakes. Early readmissions have significant financial implications for hospitals and most readmission complications are preventable if the risk of readmission is identified and managed at discharge. For example, patients requiring prolonged periods of intensive care and mechanical ventilation or complications of pneumonia are at high risk for hospital readmission. Stroke and heart disease patients have high rates of early readmission. Accordingly, a laboratory test that can be used at the time of discharge to aid in the identification of patients at risk of readmission would be highly desirable. The method of the invention may provide such a test.

In particular, the ORP of patients who are, who are suspected of being, or who are likely to become, readmitted would be determined at the time of discharge. An ORP level of a patient that is statistically the same as, or lower than, that of normals would indicate that oxidative stress is not present and that the patient can be discharged. An ORP level that is significantly higher than that of normals would indicate the presence of oxidative stress and that the patient should not be discharged or will require additional treatment after discharge. Such additional treatment after discharge may include referral to extended stay care or early disease management programs at home. These programs can reduce early readmission rates and often include nurse contact within 24 hours after discharge and frequent home check-ups for proper medication compliance and rehabilitation treatments. ORP measurements could also be used to monitor discharged patients for a period determined by the patient's physician (typically 30 days) to evaluate the effectiveness of treatments. An ORP level that decreases with treatment would indicate that the patient is improving and that the treatment is working. An ORP level that increases despite treatment would indicate that the patient is getting worse and that more aggressive treatment, additional treatment and/or a different treatment is needed. An ORP level that has decreased to the point where it is no longer significantly higher than that of normals would indicate that the patient no longer needs monitoring. Of course, the ORP level is only one diagnostic parameter, and it should be used in combination with other symptoms, results of physical examinations and the results of any other laboratory tests, to determine the proper treatment for a patient.

The method of the invention should also be useful in the diagnosis, evaluation and monitoring of patients who are suffering from, or who are suspected of having a variety of diseases, including aging diseases (e.g., arthritis, diabetes, cataracts, macular degeneration and prostate problems), cancer (e.g., prostate cancer, breast cancer, lung cancer, colorectal cancer, bladder cancer, uterine cancer, ovarian cancer, lymphoma, skin cancer, stomach cancer, liver cancer, wasting disease and cancer therapy), cognitive dysfunction (e.g., post-surgical, post-seizure, and neurodegenerative diseases), diabetes and its complications (including retinopathy, nephropathy and peripheral neuropathy), digestive diseases (e.g., inflammatory bowel disease, ulcerative colitis, Crohn's disease, gastritis, stomach cancer, pancreatitis and ulcers), drug reactions and toxicology (e.g., drug overdose and Tylenol toxicity), eye diseases (e.g., cataracts, glaucoma and macular degeneration), ear diseases (e.g., hearing loss, ear infections and sinusitis), immunological diseases (e.g., allergies, chronic fatigue syndrome and autoimmune diseases), inflammatory diseases, liver diseases (e.g., toxic hepatitis, viral hepatitis, chronic hepatitis and cirrhosis), lung diseases (e.g., asthma, bronchitis, emphysema, pneumonia, cystic fibroses, pulmonary fibroses, chronic obstructive pulmonary disease (COPD) and adult respiratory distress syndrome (ARDS)), male problems (e.g., prostate enlargement, prostate cancer, and infertility), metabolic syndrome, mouth diseases (e.g., gingivitis and periodontal disease), neurodegenerative diseases (e.g., Parkinson's disease, Alzheimer's disease, multiple sclerosis, schizophrenia, dementia and Huntington's disease), oxidative stress (e.g., due to hypertension, hyperlipidemia or altitude sickness), post-surgical complications (e.g., hypotension and shock), pregnancy diseases (e.g., high risk, pre-eclampsia, eclampsia, hypertension, toxemia and diabetes), renal diseases (e.g., kidney failure, renal toxicity, uremia and oxidative stress from dialysis), upper respiratory tract diseases, skin disorders (e.g., psoriasis, eczema, systemic lupus erythematosis, vasculitis, polymyositis, mycosis fungoides, scleroderma, pemphigoid, atopic dermatitis, contact dermatitis, sebborrheic dermatitis, dermatitis, herpetiformis, acne conglobata, acne vulgaris and UV radiation skin damage), and shock. In connection with transplants of organs, tissue or cells, the method of the invention can be used to evaluate the donor of the transplant, the transplant itself, the recipient of the transplant before the transplant, and/or to monitor whether transplant rejection is occurring or likely to occur after the transplant. For instance, an ORP level in a recipient which is significantly higher than that of normals indicates the presence of oxidative stress, and such a recipient should not receive the transplant, should be transplanted with an organ, tissue or cells that contain lower levels of oxidant species, or the recipient, transplant or both should be treated to reduce the ORP level (i.e., treated to reduce the level of oxidative stress). The ORP level of a transplant may be less critical for recipients who have an ORP level that is statistically the same as, or lower than, that of normals, since such a level indicates that oxidative stress is not present in the recipient. Other uses of the method of the invention include monitoring of anesthesia and post-anesthesia complications, life insurance risk stratification, monitoring dialysis, and evaluation and monitoring of nutrition and wellness.

The use of banked blood products is a common practice employed by the medical community worldwide for obvious beneficial reasons. However, there is a risk of adverse side effects from the transfusion of blood products into patients, including the possible development of transfusion-related acute lung injury (TRALI), multiple organ failure (MOF), and acute respiratory distress syndrome (ARDS). Brittingham et al., *J. Am. Med. Assoc.*, 165:819-825 (1957); Sauaia et al., *Arch. Surg.*, 129:39-45 (1994); Miller et al., *Am. Surg.*, 68:845-850 (2002). It would be desirable to have a means of avoiding or reducing these side effects.

The method of the invention provides such a means, and the method of the present invention has been found useful in monitoring and evaluating stored (banked) blood products. Blood products that can be monitored and evaluated according to the present invention include whole blood, packed red blood cells, platelets and fresh frozen plasma. In particular, using the method of the present invention, it has been found the ORP of stored blood products increases with the time of storage. For example, packed red blood cells have a significantly increased ORP on day 42 as compared to day 1. An increased ORP indicates an increased level of oxidants in the blood product, and the increased level of oxidants may contribute to the development of side effects in patients receiving the blood product, since transfusion of such a blood product would be expected to increase the level of oxidants and oxidative stress in the patient.

The method of the invention is also useful in monitoring and evaluating patients who will receive stored blood products. In particular, an ORP level in such a patient which is significantly higher than that of normals indicates the presence of oxidative stress, and such a patient should not be transfused or should be transfused with blood products that contain lower levels of oxidant species (i.e., a blood product that has a lower ORP level, preferably the same as that of fresh blood product). The ORP level of a blood product may be less critical for patients who have an ORP level that is statistically the same as, or lower than, that of normals, since such a level indicates that oxidative stress is not present. Determining the oxidative status of the patient and of the blood product should result in a decrease in transfusion-related side effects.

Exercise is associated with an enhanced aerobic and/or anaerobic metabolism which results in an increased formation of reactive oxygen species (ROS). Strenuous exercise, excessive exercise and overtraining generate ROS to a level that can overwhelm antioxidant defense systems. See Sen, Sports Med., 31:891-908 (2001); Margonis et al., Free Radical Biol. Med., 43(6):901-910 (Sep. 15, 2007); Gomez-Cabrera et al., Free Radical Biol. Med., 44(2):126-131 (2008); Radak et al., Aging Res. Rev., 7(1):34-42 (2008). The result is oxidative stress, and oxidative stress can cause extensive molecular, cellular and tissue damage. One possible outcome is oxidative damage to muscle tissues. Preventing or reducing muscle tissue damage during exercise training should help optimize the training effect and eventual performance. Regular exercise of moderate intensity and duration, while generating ROS, also induces an improvement in natural antioxidant enzymes and proteins and upregulation of antioxidant defense systems. See Ji, Proc. Soc. Exp. Biol. Med., 222:283-292 (1999); Rahnama et al., J. Sports Med. Phys. Fitness, 47:119-123 (2007); Gomez-Cabrera et al., Free Radical Biol. Med., 44(2):126-131 (2008); Ji, Free Radical Biol. Med., 44:142-152 (2008); Radak et al., Aging Res. Rev., 7(1):34-42 (2008). These adaptations result in decreased oxidative challenge to the body and maintenance of the oxidant-antioxidant homeostasis. Further, it appears that exercise-induced modulation of the redox state is an important means by which exercise benefits the body, increasing the resistance against, and facilitating recovery from, oxidative stress. Radak et al., Appl. Physiol. Nutr. Metab., 32:942-946 (2007); Radak et al., Free Radical Biol. Med., 44:153-159 (2008). From the foregoing, it can be seen that the maximum benefits of exercise can be realized from exercise that does not cause oxidative stress, and that exercise that does cause oxidative stress is to be avoided, whenever possible.

The method of the invention can be used to monitor and evaluate exercise performance in patients. The ORP of patients before and after, before and during, or before, during and after exercise is measured. An ORP level of a patient during or after exercise that is statistically the same as, or lower than, that of the patient before exercise indicates that oxidative stress is not present. Such an ORP level indicates that the exercise need not be changed. An ORP level of a patient during or after exercise that is significantly higher than that of the patient before exercise indicates the presence of oxidative stress. Such an ORP level indicates that the exercise may be causing damage and should be changed in some way, such as changing the frequency of the exercise, length of the exercise or even the type of exercise. As can be seen, monitoring the ORP of a patient can result in the design of an optimum exercise program for the patient so that the patient can achieve his/her desired physical fitness goals without experiencing the adverse effects and damage caused by oxidative stress.

EXAMPLES

Example 1

Diagnosis of Acute Myocardial Infarction

Whole blood was collected from normal subjects and patients with acute myocardial infarction (AMI) by venipuncture using a Vacutainer™ containing sodium heparin (Becton Dickinson, Franklin Lakes, N.J., USA). Plasma was aliquoted in 1 mL quantities and stored at −80° C. for future use.

Oxidation-reduction potential (ORP) measurements were recorded using a micro Pt/AgCl combination MI-800/410 cm Redox Electrode (Microelectrodes, Inc., Bedford, N.H., USA) connected to an HI4222 pH/mV/Temperature bench meter (Hanna Instruments, Woonsocket, R.I., USA). The electrode was immersed in a plasma sample, and a steady-state ORP reading in millivolts (mV) was recorded.

The results are presented in Table 1 below. The data were analyzed using student's two-tailed t test assuming uneven variances. As can be seen from Table 1, the ORP of the plasmas from AMI patients was significantly different than that of the plasmas from normals. Thus, a plasma ORP measurement can be used as an aid in distinguishing patients who are actually experiencing an AMI from those whose AMI-like symptoms are due to another cause.

TABLE 1

| Sample # | ORP |
|---|---|
| AMI Plasmas | |
| GR-358 | −24.5 |
| GR-379 | −30.5 |
| GR-397 | −34.0 |
| GR-1266-05 | −15.0 |
| GR-1328 | −4.1 |
| GR-1435-02 | −11.7 |
| Average: | −20.0 |
| SD: | 11.6 |
| Normal Plasmas | |
| GR-1347-02 | −41.7 |
| GR-1425 | −65.3 |
| GR-1426 | −52.6 |
| GR-1427 | −52.7 |
| GR-1428 | −59.2 |
| GR-1429 | −55.3 |
| GR-1430 | −53.2 |
| GR-1431 | −58.4 |
| GR-1432 | −30.6 |
| GR-1433 | −50.9 |
| Average: | −52.0 |
| SD: | 9.7 |
| Comparison AMI samples with normal samples | |
| p-value | 0.0003 |

Example 2

Monitoring and Identifying Critically Ill Trauma Patients

The oxidation-reduction potential (ORP) in a biological system is an integrated measure of the balance between total pro- and antioxidant components of the system. In plasma, many constituents contribute to the ORP. Reactive oxygen species (ROS), such as the superoxide ion, hydroxyl radical, hydrogen peroxide, nitric oxide, peroxynitrite, transition metal ions, and hypochlorous acid, contribute to the oxidative potential. Plasma antioxidants include thiols, vitamin C, tocopherol, β-carotene, lycopene, uric acid, bilirubin, and flavinoids. Enzymes, such as SOD, catalase, and glutathione peroxidase, are involved in the conversion of ROS into less reactive species. ORP monitoring of plasma provides a single measurement that integrates the overall quantitative balance among the pro- and antioxidant components of the system, and the ORP level is an indicator of a patient's overall oxidative status.

Critically ill patients suffer from oxidative stress, reflecting an imbalance in favor of the pro-oxidant components in the intra- and extracellular environments. The biological consequences of this imbalance favor certain chemical reactions which could be both beneficial and detrimental to the system depending upon the system involved and the disease process. Previous attempts at assessing the redox status of critically ill patients have been limited to measurements of single parameters, such as concentrations of individual antioxidants (Goode et al., *Crit. Care Med.*, 23:646-51 (1995)) or amount of lipid peroxidation (Rana et al., *Mol. Cell Biochem.*, 291: 161-6 (2006)). Although these parameters could be helpful, they might not give the clinician a complete assessment of the amount of oxidative stress occurring in a critically ill patient. Additionally, the measurement of these various parameters would prove to be laborious, time consuming, and, hence, impractical in the clinical setting. Here, a method is described that measures the overall oxidative status of critically ill trauma patients using an electrode that measures ORP in the plasma of the patients on a possible real-time basis.

Materials And Methods

This study received approval by the HCA-HealthOne Institutional Review Board according to the guidelines published by the HHS Office for Protection from Research Risk. Blood was collected from normal subjects (N=10) and critically ill patients who had suffered severe traumas (N=39) by venipuncture using a Vacutainer™ containing sodium heparin (Becton Dickinson, Franklin Lakes, N.J., USA). For critically ill patients, blood was collected on an almost daily basis until discharge. Plasma was aliquoted in 1 mL quantities and stored at −80° C. for future use. Patient demographics are listed in Table 2.

TABLE 2

|  | Patients | Controls |
|---|---|---|
| Number (n) | 39 | 10 |
| Age | 43.8 yrs ± 2.7 SEM | 46.4 yrs ± 3.5 SEM |
| Sex | 31 males<br>8 females | 7 males<br>3 females |
| Injury Severity Score (ISS) | 30.7 ± 2.4 SEM | N/A |

Oxidation-reduction potential (ORP) measurements were recorded at room temperature using a micro Pt/AgCl combination MI-800/410 cm Redox Electrode (Microelectrodes, Inc., Bedford, N.H., USA) connected to an HI4222 pH/mV/ Temperature bench meter (Hanna Instruments, Woonsocket, R.I., USA). Plasma samples were thawed, and the ORP electrode was immersed in the plasma. A reading was recorded in millivolts (mV) after the ORP value was stable for 5 seconds.

Total protein was quantified in all plasma samples using the bicinchoninic acid protein assay (Pierce Biotechnology, Rockford, Ill., USA). All plasma samples were diluted 1:100 with 1× phosphate-buffered saline, pH 7.4, prior to application to a 96-well plate. All samples were analyzed in duplicates.

Paraoxonase (PON) is a calcium-dependent aryl esterase (AE) present in plasma. When PON is associated with high density lipoproteins (HDL), an antioxidant effect against lipid peroxidation has been observed (Ferretti et al., *Biochim. Biophys. Acta*, 1635:48-54 (2003)). Indeed, a lower PON activity has been associated with a higher susceptibility of HDL to peroxidation in patients affected by diseases characterized by increases in oxidative damage (Ferretti et al., *J. Clin. Endocrinol. Metab.*, 89:2957-2962 (2004); Ferretti et al., *J. Clin. Endocrinol. Metab.*, 90:1728-1733 (2005)).

Plasma PON-AE activity was measured as previously described. Ahmed et al., *J. Biol. Chem.*, 280:5724-5732 (2005). Briefly, plasma was diluted 1:20 with 1× phosphate-buffered saline, pH 7.4. Diluted plasma was then combined 1:1 with 4 mM para-nitrophenolacetate (Sigma-Aldrich, St. Louis, Mo.) in a 96-well plate in duplicates. The plate was immediately read on a pre-warmed (37° C.) plate reader (FL600 Microplate Fluorescence Reader, Bio-Tek Instruments Inc., Winooski, Vt.) set at 410 nm. Absorbance readings were taken every 2 minutes for 20 minutes. The slope of the linear portion of the kinetic plot ($R^2 \geq 0.99$) was used to generate PON-AE activity. PON-AE activity was normalized to plasma protein. PON-AE activity is reported in units (U), where a unit equals the change in milli-absorbance units at 410 nm per minute per mg of total plasma protein.

The ORP, PON-AE and total protein data were analyzed using Matlab R14 (Mathworks, Natick, Mass.). A one-way ANOVA was used to compare all patient data versus normal data to test for significant differences with a Tukey-Kramer correction for multiple comparisons with a significance level of 0.05. All data are reported as ±standard error of the mean (SEM).

Results and Conclusions

Plasma was collected from critically ill patients who had suffered severe traumas from the time of admission until discharge. ORP was measured in the complete series of plasma samples collected from a particular patient after the patient was discharged in order to limit any day-to-day variability in the ORP electrode.

A rapid increase in ORP was observed for all of the patients after an initial ORP reading of −19.9 mV (±3.0 SEM) on admission. The admission ORP value is significantly higher than that of normal plasmas (−52.0 mV±3.1 SEM, $p<0.05$). The ORP maximum, reached at day 6 (±0.5 SEM), was significantly higher than the admission value, with a value of +13.7 mV (±2.5 SEM). The ORP maximum was also significantly higher than normal plasmas (−52.0 mV±3.1 SEM, $p<0.05$). During the remaining course of the hospitalization, the ORP of the plasma of these severely traumatized patients steadily approached the ORP of normal plasma. At the time of discharge, the ORP of plasma obtained from the severely traumatized patients was not significantly different from that of normal plasma (−52.0 mV±3.1 SEM).

For method validation purposes, PON-AE activities and total protein levels were measured. PON-AE activities were significantly higher in the admission samples (740.0 U/mg protein±20.2 SEM) compared to the ORP maxima samples (649.1 U/mg protein±18.8 SEM). Thus, the results show a correlation between trauma and a decrease in PON-AE activity. Similarly, protein levels were higher in the admission samples (47.3 mg/ml±1.6 SEM) compared to the ORP maxima samples (41.6±1.3 SEM).

The presence of markers of oxidative stress in critically ill patients is associated with a poor prognosis (Roth et al., *Curr. Opin. Clin. Nutr. Metab. Care*, 7:161-8 (2004)). However, no single parameter can accurately predict the overall redox status for a critically ill patient. The laborious performance of multiple assays for the quantification of pro-oxidants and antioxidants is not practical in a clinical setting. Therefore, a quick and simple diagnostic test is warranted.

Here, the oxidation-reduction potential (ORP) of plasma collected on consecutive days from critically ill, traumatized patients was measured from hospital admission until the time of discharge. Daily ORP levels correlated with clinical events recorded in the medical records of each particular patient, with increases in ORP indicating a worsening of a patient's condition and decreases in ORP indicating an improvement in a patient's condition. Accordingly, monitoring ORP should be a useful tool for assessing and monitoring the presence and degree of oxidative stress, the severity of injury, a patient's prognosis, and the efficacy of treatment(s). ORP monitoring could be used to determine the appropriate clinical conditions and timing that warrant treatment (e.g., administration of antioxidants) of trauma patients. In particular, ORP monitoring could be used to aid in the identification of patients who are critically ill and those who need more aggressive treatment than may be indicated by their symptoms and other diagnostic test results.

Example 3

ORP of Plasmas Before and After Exercise

The purpose of this experiment was to determine if exercise had an effect on oxidation-reduction potential (ORP) in plasma. Whole blood was collected from members of a women's college soccer team before and after exercise. The exercise consisted of an intense one-hour cardiovascular workout. The blood was collected by venipuncture using a Vacutainer™ containing sodium heparin (Becton Dickinson, Franklin Lakes, N.J., USA). Blood tubes were centrifuged at 2000 rpm for 10 minutes, and plasma was collected and aliquoted in 1 mL quantities and stored at −80° C. for future use.

The plasma samples were thawed at room temperature. ORP measurements were recorded using an MI-800/410 cm Redox Electrode (Microelectrodes, Inc., Bedford, N.H., USA) connected to an HI4222 pH/mV/Temperature bench meter (Hanna Instruments, Woonsocket, R.I., USA). The electrode was immersed in a plasma sample, and a steady-state ORP reading in millivolts (mV) was recorded.

The results are presented in Table 3 below. As can be seen from Table 3, the ORP of the plasmas of these high performance athletes decreased after exercise.

TABLE 3

| Patient Sample | Exercise | ORP (mV) | Change (+/−) |
|---|---|---|---|
| GR 1814-01 | No | −39.4 | |
| GR 1814-02 | Yes | −46.0 | −6.6 |
| GR 1815-01 | No | −35.5 | |
| GR 1815-02 | Yes | −38.3 | −2.8 |
| GR 1816-01 | No | −40.7 | |

TABLE 3-continued

| Patient Sample | Exercise | ORP (mV) | Change (+/−) |
|---|---|---|---|
| GR 1816-02 | Yes | −44.4 | −3.7 |
| GR 1817-01 | No | −49.5 | |
| GR 1817-02 | Yes | −49.2 | +0.3 |
| Average change | | | −3.2 |

Example 4

ORP of Plasma from Critically-Ill Patient Suffering Viral Infection

Patient GR-1029 was admitted to the intensive care unit of Swedish Hospital, Englewood, Colo. with flu-like symptoms, pneumonia and respiratory failure triggered by exposure to rat droppings and urine while cleaning the cage of a pet rat. The patient was diagnosed as likely having a viral infection transmitted by rodents.

This study received approval by the HCA-HealthOne Institutional Review Board according to the guidelines published by the HHS Office for Protection from Research Risk.

Blood was collected from this patient on several days during his hospitalization (see Table 4 below) by venipuncture using a Vacutainer™ containing sodium heparin (Becton Dickinson, Franklin Lakes, N.J., USA). Plasma was aliquoted in 1 mL quantities and stored at −80° C. for future use.

The plasma samples were thawed at room temperature. ORP measurements were recorded using an MI-800/410 cm Redox Electrode (Microelectrodes, Inc., Bedford, N.H., USA) connected to an HI4222 pH/mV/Temperature bench meter (Hanna Instruments, Woonsocket, R.I., USA). The electrode was immersed in a plasma sample, and a steady-state ORP reading in millivolts (mV) was recorded.

The results are presented in Table 4 below. As can be seen from Table 4, ORP was highest during the first 8 days after admission and then declined until the patient was discharged, in a similar manner to critically ill trauma patients (see Example 2). However, the ORP level for patient GR-1029 did not return to normal levels (−52.0 mV±3.1 SEM) before discharge. The ORP levels correlated with clinical events recorded in the medical records of the patient, with increased ORP levels indicating a worsening of the patient's condition and decreased ORP levels indicating an improvement in the patient's condition.

TABLE 4

| TIME (days) | ORP (mV) |
|---|---|
| 1.0 | 73.0 |
| 1.5 | 78.8 |
| 8.0 | 59.5 |
| 9.0 | 36.6 |
| 10.0 | 60.6 |
| 11.0 | 17.7 |
| 12.0 | 33.6 |
| 16.0 | 3.8 |
| 22.0 | −13.2 |
| 23.0 | −12.4 |
| 24.0 | −26.3 |
| 25.0 | −14.0 |
| 26.0 | 1.7 |
| 30.0 | −34.2 |
| 31.0 | −20.9 |
| 33.0 | −7.8 |
| 36.0 | −9.5 |
| 37.0 | −15.8 |
| 38.0 | −20.0 |

Example 5

Monitoring of Stored Blood Product (PBRC)

Transfusion-related acute lung injury (TRALI) is an adverse effect of transfusion and is the leading cause of transfusion-related death. Silliman et al., *Blood,* 105:2266-2273 (2005). Longer storage times of packed red blood cells (PBRCs) and other blood products have been associated with an increased risk in developing TRALI in transfused patients. See Biffl et al., *J. Trauma,* 50:426-432 (2001).

A total of 10 transfusion bags containing PBRCs stored in adenine, citrate and dextrose (ACD) buffer at 4° C. according to American Association of Blood Banks criteria were obtained from Bonfils Blood Center (Denver, Colo.). At Bonfils, a sample of each bag of PBRCs was collected on storage days 1 and 42. Samples were immediately centrifuged at 1000 g at 4° C. for 10 minutes, and the supernatants were collected and stored at −80° C. until further analysis.

Oxidation-reduction potential (ORP) was measured at room temperature in both the day 1 and day 42 sample supernatants. ORP measurements were recorded using a micro Pt/AgCl MI-800/410 cm Redox Electrode (Microelectrodes, Inc., Bedford, N.H., USA) connected to an HI4222 pH/mV/Temperature bench meter (Hanna Instruments, Woonsocket, R.I., USA). The electrode was immersed in a sample supernatant, and a steady-state ORP reading in millivolts (mV) was recorded.

The results are presented in Table 5 below. A student t-test was used to compare day 1 versus day 42 data to test for significant differences (p<0.05, Microsoft Excel). As can be seen, ORP was significantly increased (p<0.05) in the day 42 samples (98.1 mV±21.9 SD) as compared to the day 1 samples (62.6 mV±21.5 SD).

For method validation purposes, protein oxidation in the sample supernatants was determined by measuring plasma proteins in the supernatants by mass spectrometry (MS). Sample supernatants were analyzed by HPLC (Waters 2795 Separations Module, Milford, Mass., USA) coupled to positive electrospray ionization time of flight mass spectrometry (+ESI-TOF MS, LCT, Micromass, UK) using a method described previously. Bar-Or et al., *Crit. Care Med.,* 33:1638-1641 (2005). 10 μL of each sample was injected onto a YMC-Pack Protein-RP HPLC column (Waters, Milford, Mass., USA) heated to 50° C. A 20-minute linear gradient from 10 to 40% B using water/0.1% trifluoroacetic acid (A) and AcN/0.1% TFA (B) was utilized with a flow rate of 1 mL/min. For each plasma protein detected, the MS spectrum was deconvolved to the uncharged, parent mass using MaxEnt 1 software (Micromass, UK). The parent mass spectrum was then integrated and relative proportions of each species were calculated using an advanced, proprietary MS integration software package developed in-house.

Oxidation modifications of human serum albumin (HSA) include cysteinylation of cysteine 34 and dehydroalanine (DHA) modification of lysine 487. The percentage of oxidized HSA species increased significantly in the supernatants from day 1 (44.1%±6.9 SD) to day 42 (72.1%±8.4 SD).

Other plasma proteins identified in the supernatants by MS were α-chain of hemoglobin (αHb), β-chain of hemoglobin (βHb), apolipoprotein Al (ApoAl) and transthyretin (TTR). Significantly higher levels of oxidation modifications of αHb, βHb and TTR were observed in the day 42 supernatants as compared to the day 1 supernatants (p<0.05). Also, for αHb and ApoAl, species which had a cleaved C-terminal amino acid were observed, indicating the presence of carboxypeptidase activity, a marker of inflammation.

The data demonstrate the presence of an oxidative environment in PBRCs, which increases with storage time. This could partially explain the increased risk of developing TRALI related to the transfusion of older blood products.

Accordingly, the ORP of PBRCs and other stored blood products should be monitored, and the ORP of patients that are to receive the blood products should also be monitored. A patient that has significant oxidative stress (i.e., has a high ORP level) should be transfused with fresher blood products that contain less pro-oxidant species (i.e., has a lower ORP level). Taking the oxidative status of the patient and of the blood product into account should result in a decrease in transfusion-related risk factors such as TRALI.

TABLE 5

| PBRC Sample No. | Day 1 ORP (mV) | Day 42 ORP (mV) |
| --- | --- | --- |
| 054A | 41.4 | 88.5 |
| 056A | 48.9 | 113.8 |
| 057A | 105.2 | 124.6 |
| 058A | 77.4 | 131.2 |
| 059A | 70.3 | 115.5 |
| 060A | 88.0 | 100.7 |
| 061A | 48.8 | 80.6 |
| 062A | 52.2 | 73.5 |
| 063A | 46.8 | 75.2 |
| 064A | 46.7 | 77.1 |
| Average: | 62.6 | 98.1 |
| Standard deviation (SD) | 21.5 | 21.9 |
| Standard error of the mean (SEM) | 6.8 | 6.9 |
| p-value | 0.0018 | |
| % Change | +56.7% | |

Example 6

Monitoring and Identifying Traumatic Brain Injury Patients

In this experiment, the overall oxidative status of patients with isolated, traumatic brain injuries (ITBI) was determined by measuring the oxidation-reduction potential (ORP) of the plasma of the patients. The ITBI patients had no other major non-head traumas, such as injuries to major organs. For comparison purposes, demographically similar traumatized patients with no head injuries were included in the study.

Serial whole blood samples were obtained from severe ITBI patients (Abbreviated Injury Score (AIS)≧3, N=32) and demographically similar non-head injury traumatized patients (N=26) on an almost daily basis until discharge from the hospital, beginning with a sample collected within 24 hours of the initial injury (i.e., admission sample). Whole blood was also collected from patients with minor to moderate ITBI (AIS≦2, N=18) and healthy volunteers (N=22). Plasma was aliquoted in 1 mL quantities and stored at −80° C. for future use.

ORP measurements were recorded at room temperature using a micro Pt/AgCl combination MI-800/410 cm Redox Electrode (Microelectrodes, Inc., Bedford, N.H., USA) connected to an HI4222 pH/mV/Temperature bench meter (Hanna Instruments, Woonsocket, R.I., USA). Plasma samples were thawed, and the ORP electrode was immersed in the plasma. A reading was recorded in millivolts (mV) after the ORP value was stable for 5 seconds. The ORP electrode was calibrated with saturated, buffered solutions of quinhydrone (Sigma-Aldrich, St. Louis, Mo.) according to the manufacturer's specifications.

Patient demographic data is reported as mean±standard error of the mean (SEM). A student t-test was used to compare two ORP data groups to test for significant differences (p<0.05, Microsoft Excel). ORP data is reported as mean±SEM.

All patients enrolled in the study were admitted between March 2006 and December 2007 at Swedish Medical Center (Englewood, Colo.). A total of 76 trauma patients with an ITBI or non-head injuries and 22 healthy volunteers comprised the study group. TBI patients with trauma to the extremities (i.e. orthopedic concerns, etc.) were included in the ITBI groups while TBI patients with trauma to major organs were excluded from the study. Four groups were included in the study: healthy volunteers, ITBI patients with an AIS≦2, ITBI patients with an AIS≧3, and trauma patients with non-head injuries (see Table 6 below). All four groups were age-matched with statistically more females included in the healthy volunteers group. No statistically significant difference in the plasma ORP between healthy males and females were observed (data not shown). Additionally, no statistically significant difference for ISS and LOS was observed between the ITBI AIS≧3 and non-head injured groups.

TABLE 6

| | Healthy Volunteers | ITBI AIS ≦2 | ITBI AIS ≧3 | Non-Head Injury |
|---|---|---|---|---|
| Number (N) | 22 | 18 | 32 | 26 |
| Age (years) | 39.5 ± 2.1 | 43.1 ± 3.6 | 42.9 ± 3.1 | 46.1 ± 4.3 |
| Females | 18 | 8 | 7 | 9 |
| Injury Severity Score (ISS) | N/A | 6.8 ± 0.8 | 24.8 ± 2.1 | 19.3 ± 2.4 |
| Length of Stay (LOS) | N/A | 2.4 ± 0.5 | 12.6 ± 1.0 | 9.8 ± 1.2 |
| Deaths | N/A | 0 | 4 | 0 |

ORP values in plasma collected at admission from the ITBI AIS≦2 (−22.4 mV±2.9), ITBI AIS≧3 (−16.2 mV±3.1), and non-head injured groups (−24.2 mV±2.9) were significantly higher than the healthy volunteer group (−34.4 mV±2.5). No statistically significant differences were measured in the admission plasma ORP between the three trauma groups although the ITBI AIS≧3 and non-head injured groups approached significance (p=0.065).

A significant difference was observed between the ITBI AIS≧3 (+8.5 mV±3.4) and non-head injured groups (−5.2 mV±2.9) for the ORP maxima. An ORP maximum was assigned to the plasma sample with the highest ORP value for a particular patient during the course of hospitalization. The ORP maxima occurred on almost identical days for the ITBI AIS≧3 (5.8 days±0.5) and non-head injured groups (6.1 days±1.1). After the ORP maxima was reached for a particular patient, ORP values for the subsequent plasma samples steadily decreased until discharge approaching the average plasma ORP of healthy volunteers (data not shown).

These results demonstrate the presence of an oxidative environment in the plasma of traumatized patients, including especially severe ITBI patients. Therefore, monitoring ORP is a useful tool for assessing the degree of oxidative stress, inflammation, severity of injury and efficacy of treatment in ITBI patients.

We claim:

1. A method of evaluating a patient having a condition associated with oxidative stress in a hospital prior to discharge to determine whether the patient should be discharged from the hospital, wherein the patient has an elevated oxidation-reduction potential (ORP) relative to normal patients, the method comprising the following steps:
   a. measuring the oxidation-reduction potential (ORP) of a body fluid of the patient, wherein the body fluid is plasma;
   b. determining if the ORP is significantly different than the ORP of the same body fluid from normals; and
   c. discharging the patient from the hospital if the ORP is not significantly elevated compared to normals.

2. The method of claim 1 wherein the ORP is measured within the 24 hours prior to discharge of the patient from the hospital.

3. The method of claim 1, wherein the ORP is measured once per day or a plurality of times per day prior to discharge.

4. The method of claim 1, wherein the step of measuring the ORP comprises contacting an ORP electrode or redox electrode with the body fluid or tissue of the patient.

5. A method of evaluating a patient having a condition associated with oxidative stress in a hospital prior to discharge to determine whether the patient should be discharged from the hospital, wherein the patient has an elevated oxidation-reduction potential (ORP) relative to normal patients, the method comprising the following steps:
   a. contacting an oxidation-reduction potential (ORP) electrode or a redox electrode with a body fluid of the patient to measure the ORP of the body fluid within the 24 hours prior to discharge of the patient from the hospital, wherein the body fluid is plasma;
   b. determining if the ORP is significantly elevated compared to the ORP of the same body fluid from normals; and
   c. discharging the patient from the hospital if the ORP is not significantly elevated compared to normals.

* * * * *